United States Patent [19]

Naoi

[11] Patent Number: 4,944,884
[45] Date of Patent: Jul. 31, 1990

[54] BODY FLUID PURIFICATION METHOD USING ACTIVATED CARBON FIBERS OF NOVOLOID RESIN ORIGIN

[75] Inventor: Keiji Naoi, Fujinomiya, Japan

[73] Assignee: Terumo Kabushiki Kaisha, Tokyo, Japan

[21] Appl. No.: 453,361

[22] Filed: Dec. 18, 1989

Related U.S. Application Data

[60] Division of Ser. No. 300,744, Jan. 23, 1989, abandoned, which is a continuation of Ser. No. 48,057, May 11, 1987, abandoned.

[30] Foreign Application Priority Data

May 14, 1986 [JP] Japan ............................. 61-109921

[51] Int. Cl.$^5$ ............................................ B01D 15/04
[52] U.S. Cl. ............................... 210/692; 210/694; 210/502.1; 210/903; 210/908; 604/5
[58] Field of Search ............... 210/259, 317, 435, 446, 210/483, 489, 490, 491, 499, 503, 505, 508, 691, 692, 694, 903, 908, 502.1; 209/363; 604/4–6; 428/367, 408; 502/416, 418; 530/829, 830, 380, 415

[56] References Cited

U.S. PATENT DOCUMENTS 4,076,692  2/1978  Batha et al. .................... 264/331.22
4,246,107  1/1981  Takenaka et al. ............. 210/317 X
4,576,929  3/1986  Shimazaki ...................... 210/483 X

OTHER PUBLICATIONS

"Histamine Levels in Stored Human Blood", (D. B. Frewin et al.), Transfusion 1984, vol. 24, pp. 502–504.

Primary Examiner—W. Gary Jones
Attorney, Agent, or Firm—Frishauf, Holtz, Goodman & Woodward

[57] ABSTRACT

A body fluid purification method which comprises passing the body fluid through an apparatus for purifying a body fluid by removing micro-aggregates, histamine, etc, from the body fluid. This apparatus comprises a housing constituting a body fluid flow path, and a filter consisting of activated carbon fiber prepared by baking novoloid filber in steam, the filter being transversely arranged in the housing so as to cross body fluid the flow path.

3 Claims, 1 Drawing Sheet

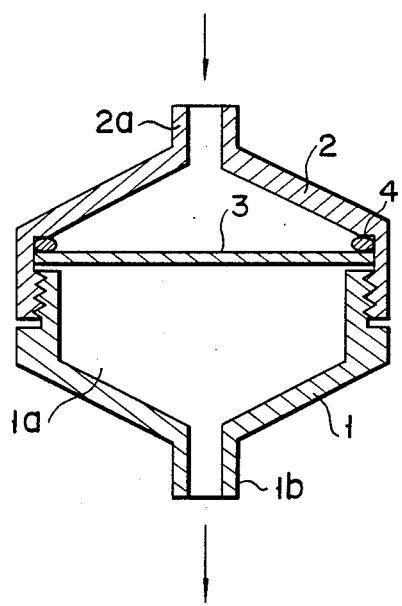

BODY FLUID PURIFICATION METHOD USING ACTIVATED CARBON FIBERS OF NOVOLOID RESIN ORIGIN

This application is a division of application Ser. No. 07/300,744, filed Jan. 23, 1989, now abandoned; which is a continuation of Ser. No. 07/048,057 filed May 11, 1987, now abandoned.

BACKGROUND OF THE INVENTION (a) Field of the Invention

The present invention relates to a body fluid purification apparatus for removing noxious substances contained in a body fluid, particularly, histamine, serotonin, and the like in long-term preserved blood, and other substances in the body fluid which are harmful to the human body.

(b) Description of the Prior Art

Conventionally, extensive studies have been made in order to preserve blood as long as possible. It has been found that when concentrated erythrocytes are preserved over a long period of time, the amounts of micro-aggregates (of, for example, blood platelets, leukocytes, and the like) and histamine increase (Frewin, D. B. et al, Transfusion, 24 (6): 502–504, 1984). Histamine is physiologically related to the contraction of a smooth muscle, exacerbation of capillary permeability, erythema, itching, stimulus of adrenal medulla, and the like. Therefore, an increase in the amount of histamine is a factor which cannot be ignored in the operation of blood transfusion. It is also known that noxious substances such as micro-thrombuses consisting of cells or proteins are produced in longterm preserved blood. Therefore, histamine and other noxious substances must be removed before blood transfusion is performed.

SUMMARY OF THE INVENTION

It is an object of the present invention to provide a body fluid purification apparatus which is suitable for efficiently removing noxious substances in a body fluid, particularly, micro-aggregates and noxious substances such as histamine, serotonin, and the like, contained in long-term preserved blood, without clogging.

As a means for achieving the above object, a body fluid purification apparatus is provided, comprising a housing constituting a body fluid flow path, and a filter consisting of activated carbon fiber, preferably, an activated carbon woven fabric or nonwoven fabric, arranged in the housing so as to traverse the body fluid flow path.

In this specification, "activated carbon fiber" corresponds to carbon fiber whose carbon portion is activated.

BRIEF DESCRIPTION OF THE DRAWING

The drawing is a sectional view of a body fluid purification apparatus according to an embodiment of the present invention.

DESCRIPTION OF THE PREFERRED EMBODIMENT

An activated carbon woven fabric or nonwoven fabric used in the present invention preferably has a pore diameter (gap) which allows blood cells to pass therethrough, but does not allow micro-aggregates (e.g., blood platelets, leukocytes, and the like) substantially larger than the blood cells to pass therethrough. Note that although histamine and serotonin are smaller than blood cells, they are caught and adsorbed in the microrecesses of the surface of the activated carbon.

In order to efficiently remove noxious microsubstances such as histamine, serotonin, and the like, the activated carbon fiber preferably has a specific surface area of 900 $m^2/g$ or more. Since a removal ratio of histamine, serotonin, and the like is preferably 95% or higher, the activated carbon woven fabric or nonwoven fabric having the above specific surface area preferably has a thickness of 3 mm or more. In this case, a single activated carbon woven fabric or nonwoven fabric can be used. Alternatively, a plurality of fabrics can be combined to obtain a desired thickness.

As the activated carbon woven fabric or nonwoven fabric, a single elongated fabric can be used. As a preferred example of the activated carbon woven fabric or nonwoven fabric, a woven fabric or nonwoven fabric consisting of novoloid fiber of a threedimensional structure represented by the following structural formula is activated and baked in steam, and the resultant woven or nonwoven fabric is then used as a filter.

NOVOLOID FIBER

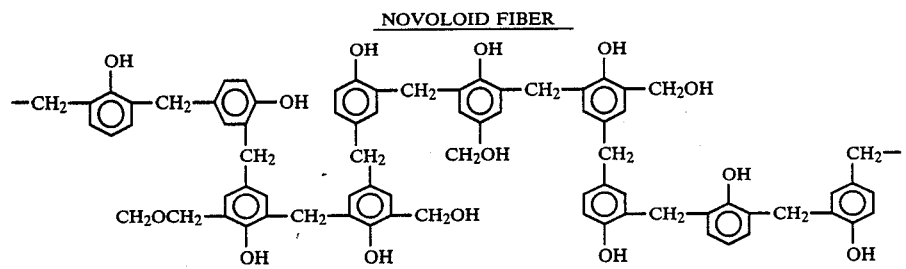

An illustrated embodiment of the present invention will now be described. In the drawing, reference numeral 1 denotes a funnel-like housing. Funnel-like cap 2 is capped and fitted in large-diameter opening 1a. Filter 3 is clamped between housing 1 and cap 2, to close opening 1a. O-ring 4 is mounted along the periphery of filter 3, and cap 2 is fastened to maintain a liquid-tight seal at the peripheral portion of filter 3.

Therefore, a body fluid to be purified is supplied from small-diameter opening 2a of cap 2, passes through filter 3, and is discharged from small-diameter opening 1b of housing 1.

A material for housing 1 and cap 2 is not limited, as long as it does not pose a problem for use in medical equipment. Preferably, a synthetic resin, e.g., polypropylene, polycarbonate, polyvinyl chloride, or the like is used. For the same reason, the material for O-ring 4 is not limited. For example, an elastomer, e.g., polyurethane rubber, can be used.

As is described above, filter 3 consists of activated carbon fiber and, preferably, a single activated carbon woven fabric or nonwoven fabric or a multilayered structure thereof, to have a thickness of 0.1 mm to several millimeters.

EXAMPLE

Tests for the removal of histamine and serotonin were conducted using a body fluid purification apparatus having substantially the same construction as that shown in the drawing, under the following conditions:

Note that housing 1 and cap 2 were made of polypropylene, and that, as filter 3, an activated carbon woven fabric having a thickness of 0.5 mm and a specific surface area of 1,500 $m^2/g$ (trade name: "ACC 509-20"; available from Gun-ei Chemical Industry Co., Ltd) obtained by activating and baking a woven fabric consisting of the novoloid fiber in steam, and an activated carbon woven fabric having a thickness of 1.0 mm and a specific surface area of 2,000 $m^2/g$ (trade name: "ACN 157-20"; available from Gun-ei Chemical Industry Co., Ltd) obtained by activating and baking a nonwoven fabric consisting of the novoloid fiber in steam, were combined, as is shown in the Table below, by changing the laminated number of fabrics. The inner diameter of large-diameter opening 1a of housing 1 was 25 mm. 10 ml of blood plasma were made to flow at a flow rate of 10 ml/min from small-diameter opening 2a of cap 2 toward small-diameter opening 1b of housing 1. This blood plasma was obtained by mixing a histamine standard solution and a Serotonin standard solution with CPD-added human blood plasma.

Histamine and Serotonin removal ratios were measured, respectively, before and after filtration, using a fluorescent photometer.

The results obtained revealed that the body fluid purification apparatus according to the present invention could remove histamine and serotonin with high efficiency.

Although not shown in the Table below, it was also found that the micro-aggregates could be similarly removed.

vated carbon particles (average particle size: 0.3~1.0 mm) (trade name: "BAC-MU-L"; available from Kureha Chemical Industries Co., Ltd.) to form a 5 mm thick layer in the housing, in place of the activated carbon woven fabric or nonwoven fabric. It was found that the surface area of the particles was relatively small, adsorption of histamine and the like was insufficient (80%), and clogging occurred easily. In addition, when an activated carbon woven fabric was stuffed in the housing, in a cotton form, the pore diameter (body fluid path gap) could not be controlled, and a stable removal ratio could not be obtained.

As has been described above, according to the body fluid purification apparatus of the present invention, since the activated carbon woven fabric or nonwoven fabric is used as the filter, substances in a body fluid which are harmful to the human body, in particular, micro-aggregates and substances which are harmful to the human body, such as histamine, serotonin, and the like in long-term preserved blood, can be efficiently and simultaneously removed.

What is claimed is:

1. A method for removing histamine or serotonin from body fluid comprising providing a housing defining a body fluid flow path and a filter consisting essentially of activated carbon fibers, arranged in said housing in a position to traverse said body fluid flow path, said activated carbon fibers being made from novoloid fibers by baking and activating said novoloid fibers;

catching and adsorbing histamine or serotonin from the body fluid by passing said body fluid along said flow path and through said filter; and recovering the body fluid from the housing.

2. The method of claim 1, wherein the activated carbon fibers have a surface area of 900 $m^2/g$, comprising catching and absorbing 95% or more of the histamine or serotonin from the body fluid.

3. The method of claim 1, wherein said filter consisting essentially of said fibers is arranged to prevent particles larger than blood cells to pass therethrough, and said filter has a specific surface area of 900 $m^2/g$ or more.

TABLE

| Filter | Histamine | | | Serotonin | | |
|---|---|---|---|---|---|---|
| | Before Filtration (ng/ml) | After Filtration (ng/ml) | Removal Ratio (%) | Before Filtration (ng/ml) | After filtration (ng/ml) | Removal Ratio (%) |
| * Woven fabric 3 | 41.64 | 19.16 | 54.0 | 1088 | 695 | 36.1 |
| Woven fabric 5 | 54.58 | 11.69 | 78.6 | 1021 | 306 | 70.0 |
| Woven fabric 7 | 32.26 | 0.53 | 98.4 | 1056 | 77 | 92.7 |
| Woven fabric 9 | 32.26 | 0 | 100 | 1056 | 11 | 99.0 |
| ** Nonwoven fabric 1 | 41.64 | 29.20 | 29.9 | 1088 | 762 | 30.0 |
| Nonwoven fabric 2 | 54.58 | 15.87 | 15.87 | 1021 | 354 | 65.3 |
| Nonwoven fabric 3 | 32.26 | 2.23 | 2.23 | 1056 | 83 | 92.1 |
| Nonwoven fabric 4 | 32.26 | 1.38 | 1.38 | 1056 | 20 | 98.1 |

(Note)
*ACC 509-20
**ACN 157-20

Following the same procedures as above, purification was performed while the housing was filled with acti-